United States Patent
Jo et al.

(10) Patent No.: US 9,366,741 B2
(45) Date of Patent: Jun. 14, 2016

(54) MEDICAL IMAGE IMAGING METHOD, MEDICAL DIAGNOSTIC APPARATUS USING THE SAME, AND RECORDING MEDIUM THEREFOR

(71) Applicants: SAMSUNG ELECTRONICS CO., LTD., Sueon-si (KR); KOREA ADVANCED INSTITUTE OF SCIENCE AND TECHNOLOGY, Daejeon (KR)

(72) Inventors: Jae-moon Jo, Seongnam-si (KR); Hyun-wook Park, Daejeon (KR); Joon-sung Choi, Daejeon (KR)

(73) Assignees: SAMSUNG ELECTRONICS CO., LTD., Suwon-si (KR); KOREA ADVANCED INSTITUTE OF SCIENCE AND TECHNOLOGY, Daejeon-si (KR)

( * ) Notice: Subject to any disclaimer, the term of this patent is extended or adjusted under 35 U.S.C. 154(b) by 416 days.

(21) Appl. No.: 13/920,666

(22) Filed: Jun. 18, 2013

(65) Prior Publication Data

US 2014/0100441 A1    Apr. 10, 2014

(30) Foreign Application Priority Data

Oct. 10, 2012 (KR) .................. 10-2012-0112661

(51) Int. Cl.
| | |
|---|---|
| G06K 9/00 | (2006.01) |
| G01R 33/56 | (2006.01) |
| G01R 33/565 | (2006.01) |
| G06T 11/00 | (2006.01) |
| A61B 5/055 | (2006.01) |
| A61B 5/00 | (2006.01) |
| G01R 33/48 | (2006.01) |

(52) U.S. Cl.
CPC ............ *G01R 33/5608* (2013.01); *A61B 5/055* (2013.01); *A61B 5/7225* (2013.01); *A61B 5/7253* (2013.01); *G01R 33/56545* (2013.01); *G06T 11/006* (2013.01); *G01R 33/4824* (2013.01)

(58) Field of Classification Search
USPC ........................................................ 382/128
See application file for complete search history.

(56) References Cited

U.S. PATENT DOCUMENTS 8,170,315 B2 *  5/2012  Mistretta ............... G06T 11/006
                                                               382/131
8,180,148 B2    5/2012  Cover et al.
(Continued)

OTHER PUBLICATIONS

O'Halloran et al, Iterative Reconstruction of Time-Resolved Images Usiing Highly Constrained Back-Projection (HYPR), Magn Reson Med 2008; 59: pp. 132-139.*

(Continued)

*Primary Examiner* — Yon Couso
(74) *Attorney, Agent, or Firm* — Sughrue Mion, PLLC

(57) ABSTRACT

A medical diagnostic apparatus includes a data obtainer, which obtains an image frame included in a region to be imaged; and a data processor, which processes the obtained frame and obtains a medical image. The data obtainer includes a composite image generator, which generates a composite image by using the image frame; and a medical image obtainer, which compensates the composite image by using the image frame and boundary conditions corresponding to image signals included in the composite image and obtains the medical image by using the compensated composite image.

20 Claims, 18 Drawing Sheets

(56) References Cited

U.S. PATENT DOCUMENTS

2007/0156044 A1 7/2007 Mistretta et al.
2007/0156045 A1 7/2007 Mistretta et al.
2008/0199063 A1* 8/2008 O'Halloran ........ G01R 33/4824
                                                          382/131

OTHER PUBLICATIONS

Communication dated Oct. 25, 2013 issued by the Korean Intellectual Property Office in counterpart Korean Patent Application No. 10-2012-0112661.
Communication dated Mar. 18, 2014 issued by the European Patent Office in counterpart European Application No. 13177627.0.
Johnson et al., "Improved Waveform Fidelity Using Local HYPR Reconstruction (HYPR LR)", Magnetic Resonance in Medicine, Mar. 1, 2008, vol. 59, No. 3, pp. 456-462, XP007909404.
Mistretta et al., "Highly Constrained Backprojection for Time-Resolved MRI", Magnetic Resonance in Medicine, Dec. 9, 2005, vol. 55, pp. 30-40, XP002404098.
O'Halloran et al., "Iterative Projection Reconstruction of Time-Resolved Images Using Highly-Constrained Back-Projection (HYPR)", Magnetic Resonance in Medicine, 2008, vol. 59, pp. 132-139.
Wang et al., "Ultrashort TE Spectroscopic Imaging Using Complex HYPR LR Reconstruction", NIH Public Access Author Manuscript, National Institute of Health, Jul. 2009, vol. 62, No. 1, 18 pgs. total.
Byrne, "Iterative algorithms for deblurring and deconvolution with constraints", Inverse Problems, vol. 14, 1998, pp. 1455-1467.

* cited by examiner

COMPLEX HYPR LR

PRESENT METHOD

COMPLEX HYPR LR

PRESENT METHOD

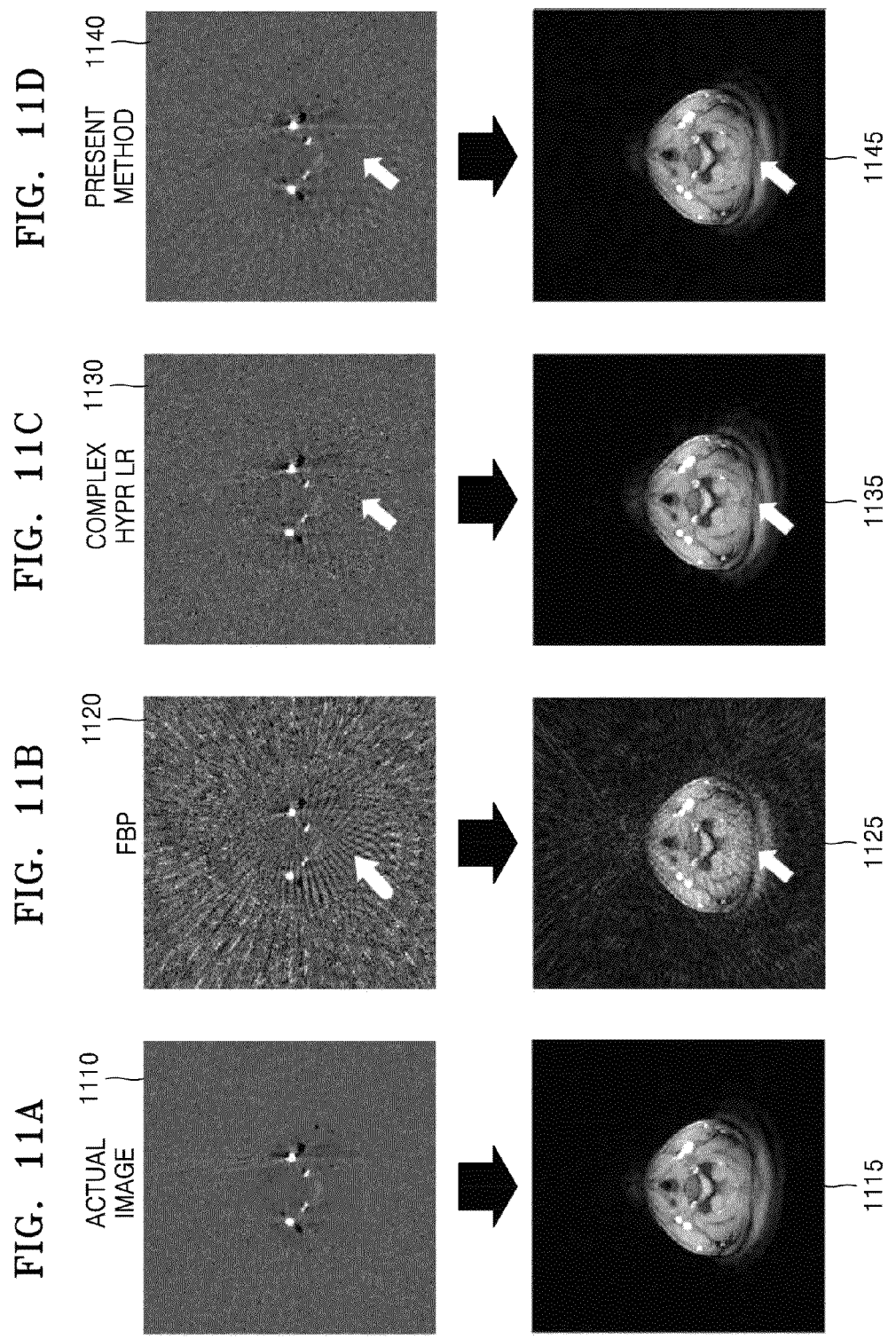

MEDICAL IMAGE IMAGING METHOD, MEDICAL DIAGNOSTIC APPARATUS USING THE SAME, AND RECORDING MEDIUM THEREFOR

CROSS-REFERENCE TO RELATED PATENT APPLICATION

This application claims the priority from Korean Patent Application No. 10-2012-0112661, filed on Oct. 10, 2012, in the Korean Intellectual Property Office, the disclosure of which is incorporated herein in its entirety by reference.

BACKGROUND

1. Field

Methods and apparatuses consistent with exemplary embodiments relate to obtaining a medical image from medical image data obtained by a medical diagnostic apparatus and a medical diagnostic apparatus using the method.

2. Description of the Related Art

Magnetic resonance imaging (MRI) is a technique for exposing a human body to a uniform magnetic field and forming an image of the human body based on data obtained via nuclear magnetic resonance. The nuclear magnetic resonance is a phenomenon that, when a particular high frequency wave is incident to the nucleus of an atom that is magnetized by an external magnetic field, the nucleus at a low energy level absorbs energy of the high frequency wave and is excited to a high energy level. In MRI, the magnetic field gradients are used to form an image by using signals projected to a human body, where projection signals are applied to a region to be imaged according to successive measuring cycles at which the magnetic field gradients are changed.

Generally, each of the measurements is referred to as a view, and the quality of an image depends on the number of views. Therefore, as the number of views per frame increases, more information regarding an object may be obtained. As a result, the quality of an image may be improved, but a period of time for obtaining the image increases. On the contrary, as the number of views per frame decreases, a period of time for obtaining an image decreases, but the quality of the image may be deteriorated.

Therefore, a method of obtaining an image frame including a small number of views within a short period of time and successfully reproducing an image therefrom is in demand.

Methods of reconstructing an image from a set of projected views include a method of obtaining projected views in the form of the Descartes lattice and reconstructing an image therefrom via a Fourier transform and a method of reconstructing an image from radially obtained projected views via Radon space transform. Compared to the former method, the latter method is advantageous for successfully reconstructing an image even in a sub-sampling environment.

A highly-constrained projection reconstruction (HYPR) method enables fast reconstruction of radial data by increasing time resolution. However, only positive data may be processed by using the HYPR method. Therefore, an image may be inaccurately reconstructed in a case of using complex data, such as phase contrast (PC) using phase data, and cross-talk may occur due to a combination with a composite image. The cross-talk refers to overlapping of an unnecessary image other than a desired image.

Therefore, methods and an apparatuses for quickly reconstructing an image at an improved accuracy are needed.

SUMMARY

Exemplary embodiments may address at least the above problems and/or disadvantages and other disadvantages not described above. Also, the exemplary embodiments are not required to overcome the disadvantages described above, and an exemplary embodiment may not overcome any of the problems described above.

One or more of exemplary embodiments provide a method of imaging a medical image for reconstructing an image with improved accuracy and high spatio-temporal resolution, a medical diagnostic apparatus using the method, and a computer-readable recording medium having recorded thereon the method.

One or more of exemplary embodiments further provide a method of imaging a medical image for accurately reconstructing a medical image including complex data, a medical diagnostic apparatus using the method, and a computer-readable recording medium having recorded thereon the method.

According to an aspect of an exemplary embodiment, there is provided an imaging method for imaging an medical image, at a medical imaging apparatus, the imaging method including obtaining at least one image frame included in a region to be imaged; generating a composite image by using the at least one image frame; compensating the composite image by using the at least one image frame and boundary conditions corresponding to image signals included in the composite image; and obtaining the medical image by using the compensated composite image.

The boundary conditions include the maximum value and the minimum value of the image signals included in the composite image, and the compensating of the composite image includes setting the maximum offset and the minimum offset, such that levels of the image signals included in the composite image have positive values, based on the maximum value and the minimum value of the image signals included in the composite image. The compensating of the composite image includes applying the maximum offset to the image frame, such that levels of image signals included in the image frame have positive values; applying the maximum offset to the composite image, such that levels of image signals included in the composite have positive values; compensating the composite image, to which the maximum offset is applied, by using the image frame, to which the maximum offset is applied; applying the minimum offset to the image frame, such that levels of image signals included in the image frame have positive values; applying the minimum offset to the composite image, such that levels of image signals included in the composite image have positive values; compensating the composite image, to which the minimum offset is applied, by using the image frame, to which the minimum offset is applied; and generating the compensated composite image by using the compensated composite image to which the maximum offset is applied and the compensated composite image to which the minimum offset is applied.

The obtaining of the medical image includes repeatedly compensating the composite image by using the image frame and the boundary conditions for a plurality of number of times, and the composite image compensated in a single compensation is updated as a composite image for a next compensation.

The composite image is compensated by using an HYPR method. The obtaining of the at least one image frame includes obtaining the at least one image frame regarding at least one radial view included in the region to be imaged.

The medical diagnostic apparatus includes an MRI apparatus, and the image frame includes complex image data.

According to an aspect of an exemplary embodiment, there is provided a medical diagnostic apparatus including a data obtainer, which obtains at least one image frame included in a region to be imaged; and a data processor, which processes the obtained at least one image frame and obtains a medical image, wherein the data processor includes a composite image generator, which generates a composite image by using the at least one image frame; and a medical image obtainer, which compensates the composite image by using the at least one image frame and boundary conditions corresponding to image signals included in the composite image and obtains the medical image by using the compensated composite image.

The boundary conditions include the maximum value and the minimum value of the image signals included in the composite image, and the medical image obtainer includes an offset setter for setting the maximum offset and the minimum offset, such that levels of the image signals included in the composite image have positive values based on the maximum value and the minimum value of the image signals included in the composite image. The medical image obtainer further includes a maximum offset applicator, which applies the maximum offset to the image frame, such that levels of image signals included in the image frame have positive values, applies the maximum offset to the composite image, such that levels of image signals included in the composite have positive values, and compensates the composite image, to which the maximum offset is applied, by using the image frame, to which the maximum offset is applied; a minimum offset applicator, which applies the minimum offset to the image frame, such that levels of image signals included in the image frame have positive values, applies the minimum offset to the composite image, such that levels of image signals included in the composite have positive values, and compensates the composite image, to which the minimum offset is applied, by using the image frame, to which the minimum offset is applied; and a compensated composite image generator, which generates the compensated composite image by using the compensated composite image to which the maximum offset is applied and the compensated composite image to which the minimum offset is applied.

The medical image obtainer repeatedly compensates the composite image by using the image frame and the boundary conditions for a plurality of number of times, and the composite image compensated in a single compensation is updated as a composite image for a next compensation.

The medical image obtainer applies an HYPR method for compensating the composite image.

The data obtainer obtains the at least one image frame regarding at least one radial view included in the region to be imaged.

The medical diagnostic apparatus includes an MRI apparatus, and the image frame includes complex image data.

According to an aspect of an exemplary embodiment, there is provided a computer-readable recording medium having recorded thereon a computer program for implementing the above-described methods.

BRIEF DESCRIPTION OF THE DRAWINGS

The above and/or other aspects of exemplary embodiments will become more apparent by describing certain exemplary embodiments, with reference to the accompanying drawings, in which:

FIGS. 11A, 11B, 11C, and 11D show comparison images obtained as a result of a third simulation.

DETAILED DESCRIPTION

Figure 1:
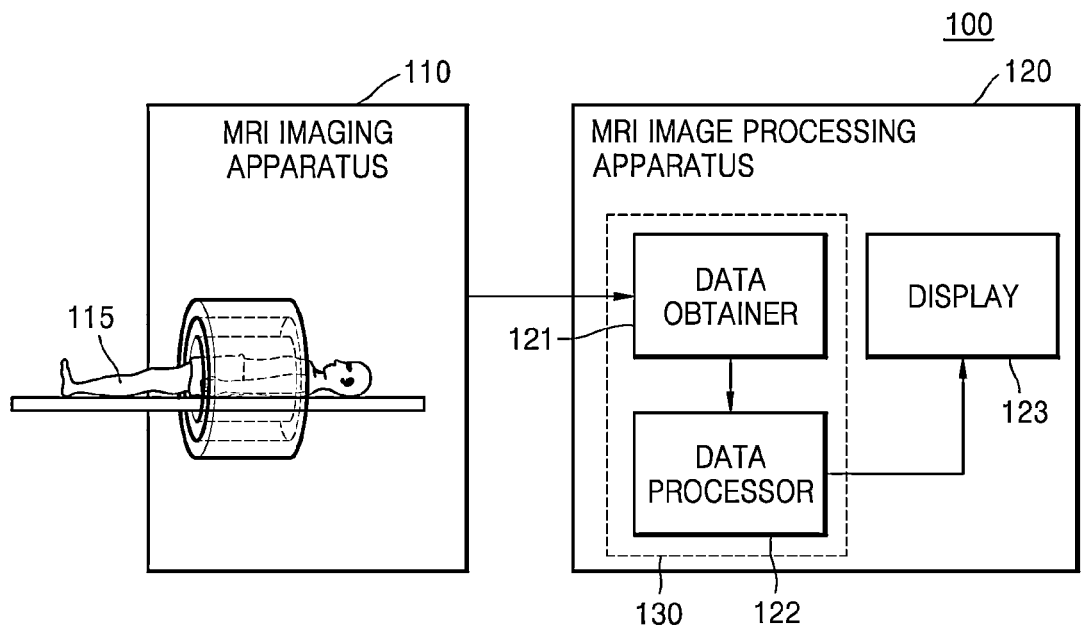
FIG. 1 is a schematic diagram showing the overall structure of an MRI system.

Below, certain exemplary embodiments are described in greater detail with reference to the accompanying drawings.

In the following description, like reference numerals are used for the like elements, even in different drawings. The matters defined in the description, such as detailed construction and elements, are provided to assist in a comprehensive understanding of exemplary embodiments. However, exemplary embodiments can be carried out without those specifically defined matters. Also, well-known functions or constructions are not described in detail since that would obscure the description with unnecessary detail.

Unless explicitly described to the contrary, the word "comprise" and variations such as "comprises" or "comprising" should be understood to imply the inclusion of stated elements but not the exclusion of any other elements.

Exemplary embodiments relate to a method of reproducing an image from radially obtained data that may be applied to medical image imaging methods for providing medical diagnosis, by reproducing images from signals projected to body tissue, as for example, in MRI, computed tomography (CT), positive electron tomography (PET), ultrasound, etc.

According to exemplary embodiments, the HYPR-based reproduction methods may be applied to imaging methods and imaging apparatuses that need to process complex data, such as phase contrast (PC) using phase data. Furthermore, errors due to cross-talk may be reduced, and thus images may be reproduced with substantially increased accuracy.

FIG. 1 is a schematic diagram showing the overall structure of an MRI system 100. The MRI system 100 includes an MRI imaging apparatus 110 and an MRI image processing apparatus 120. The MRI imaging apparatus 110 and the MRI image processing apparatus 120 may be separate apparatuses, or may be integrated with each other.

The MRI imaging apparatus 110 receives a control signal for obtaining a magnetic resonance (MR) image and is operated according to the control signal. The MRI imaging apparatus 110 receives MR signals that are used for generating an MR image corresponding to an object 115 positioned in a bore of the MRI imaging apparatus 110 and outputs the MR signals to the MRI image processing apparatus 120.

The MRI image processing apparatus 120 includes a data obtainer 121, which obtains image data received from the MRI imaging apparatus 110, and a data processor 122, which generates a medical image from the obtained data, and may include a display 123, which displays the generated medical image. For example, the image data received from the MRI imaging apparatus 110 may be MR signals generated by the MRI image processing apparatus 120.

A medical diagnostic apparatus 130 according to an exemplary embodiment may be included in the MRI image processing apparatus 120 of the MRI system 100 and may include the data obtainer 121 and the data processor 122.

A medical diagnostic apparatus according to an exemplary embodiment is described in detail below with reference to FIGS. 2A and 2B. For example, a medical diagnostic apparatus 200 may correspond to the medical diagnostic apparatus 130 of FIG. 1. However, the present exemplary embodiment is not limited to an MRI system, and may be also applied to other medical diagnostic methods and medical diagnostic apparatuses for reproducing images from the signals projected to body tissue.

Figure 2A:
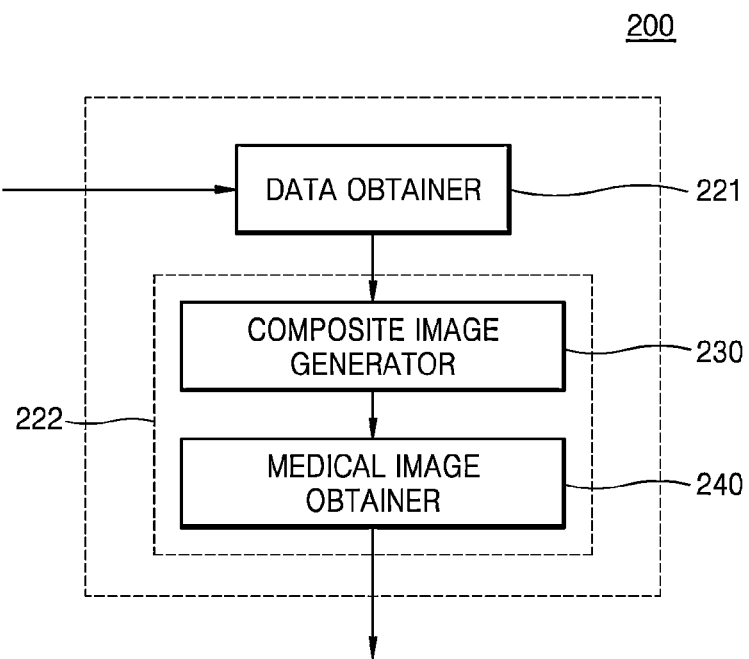
FIGS. 2A, and 2B are diagrams showing a medical diagnostic apparatus according to an exemplary embodiment.
Figure 2B:
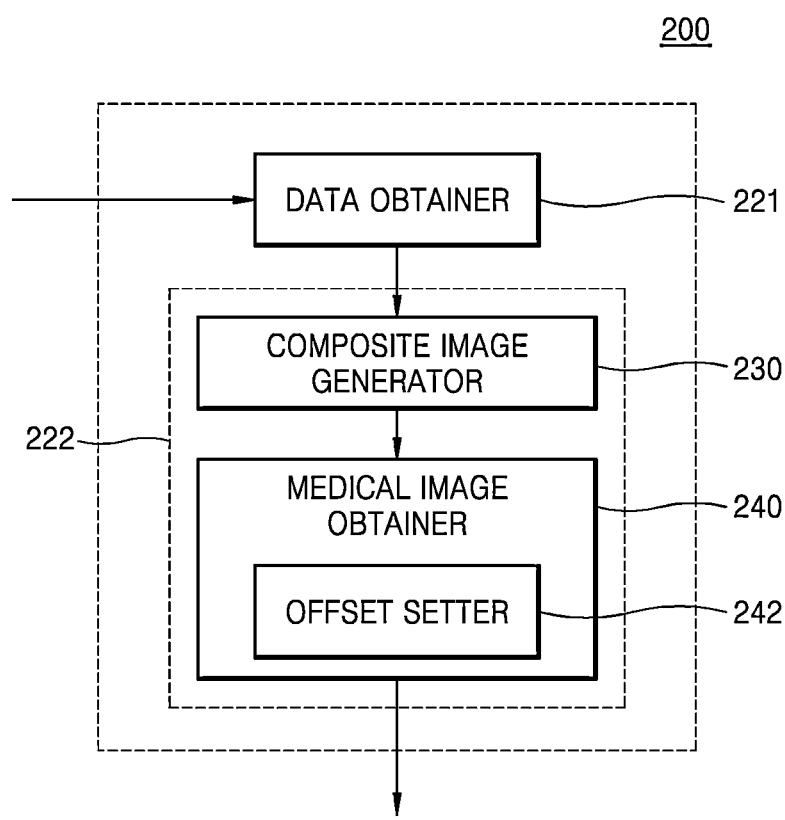

Referring to FIGS. 2A and 2B, the medical diagnostic apparatus 200 according to an exemplary embodiment includes a data obtainer 221 and a data processor 222. The data processor 222 includes a composite image generator 230 and a medical image obtainer 240. The components of the medical diagnostic apparatus 200 may be separate elements, or may be integrated with each other.

The data obtainer 221 obtains image frames in the unit of at least one view included in a region to be imaged. The image frames obtained by the data obtainer 221 are processed by the data processor 221 and are used for obtaining a medical image. Since image frames correspond to undersampled low resolution image data, the image frames may be insufficient for obtaining a final medical image of a desired quality. Therefore, in this case, at least one image frame obtained in correspondence to different views is used for obtaining a final medical image of a desired quality.

The composite image generator 230 generates a composite image by using at least one image frame, and the medical image obtainer 240 compensates the composite image by using an image frame and boundary conditions corresponding to image signals included in the composite image and obtains the medical image by using the compensated composite image.

The boundary conditions used by the medical image obtainer 240 to compensate a composite image may include the maximum value and the minimum value of image signals included in the composite image.

In the present exemplary embodiment, the boundary conditions are used to reconstruct complex data having a real part or an imaginary part having negative values. The usage of the boundary conditions is described in detail below.

When it is assumed that a predetermined image signal f is within a range of $f^L < f < f^U$ (where $f^L < 0$ and $f^U > 0$), the signals obtained as $(f + |f^L|)$ and $(|f^U| - f)$ have positive values. Therefore, if the minimum value of the obtained predetermined image signal is $f^L$ and the maximum of the predetermined image signal is $f^U$, the minimum offset $|f^L|$ and the maximum offset $|f^U|$ may be set based on the minimum value $f^L$ and the maximum value $f^U$.

For example, the predetermined image signal may be expressed as a sinogram. The sinogram represents projection data that are obtained in respective directions and sequentially arranged according to a direction of projection. A pixel value of each row of a sinogram is identical to an amplitude of each profile at a corresponding location.

Therefore, after sinograms of the minimum offset $|f^L|$ and the maximum offset $|f^U|$ are calculated and operations of addition and/or subtraction with respect to the sinograms of the predetermined image signal are performed, an image to be reconstructed has only positive values. Such a sinogram to which offsets are applied to have only positive values may be processed by using an imaging technique for processing positive data only.

Operations for obtaining image frames by using sinograms are described in detail below with reference to FIGS. 4 and 5.

The medical image obtainer 240 may include an offset setter 242, which sets the maximum offset and the minimum offset for setting levels of image signals included in a composite image to have positive values based on the maximum value and the minimum value of the image signals included in the composite image. The offset setter and the operation in which the medical image obtainer 240 compensates a composite image by using an image frame and boundary conditions are described in detail below with reference to FIG. 4.

In addition to the components shown in FIGS. 2A and 2B, the medical diagnostic apparatus 200 may further include various components. For example, the medical diagnostic apparatus 200 may further include a receiver (not shown) for receiving image data from an image capturing device (not shown), a user interface (not shown) for receiving predetermined commands or data from a user or outputting predetermined data to the user, and a storage (not shown) for storing generated medical images, other data, and image processing programs.

Figure 3:
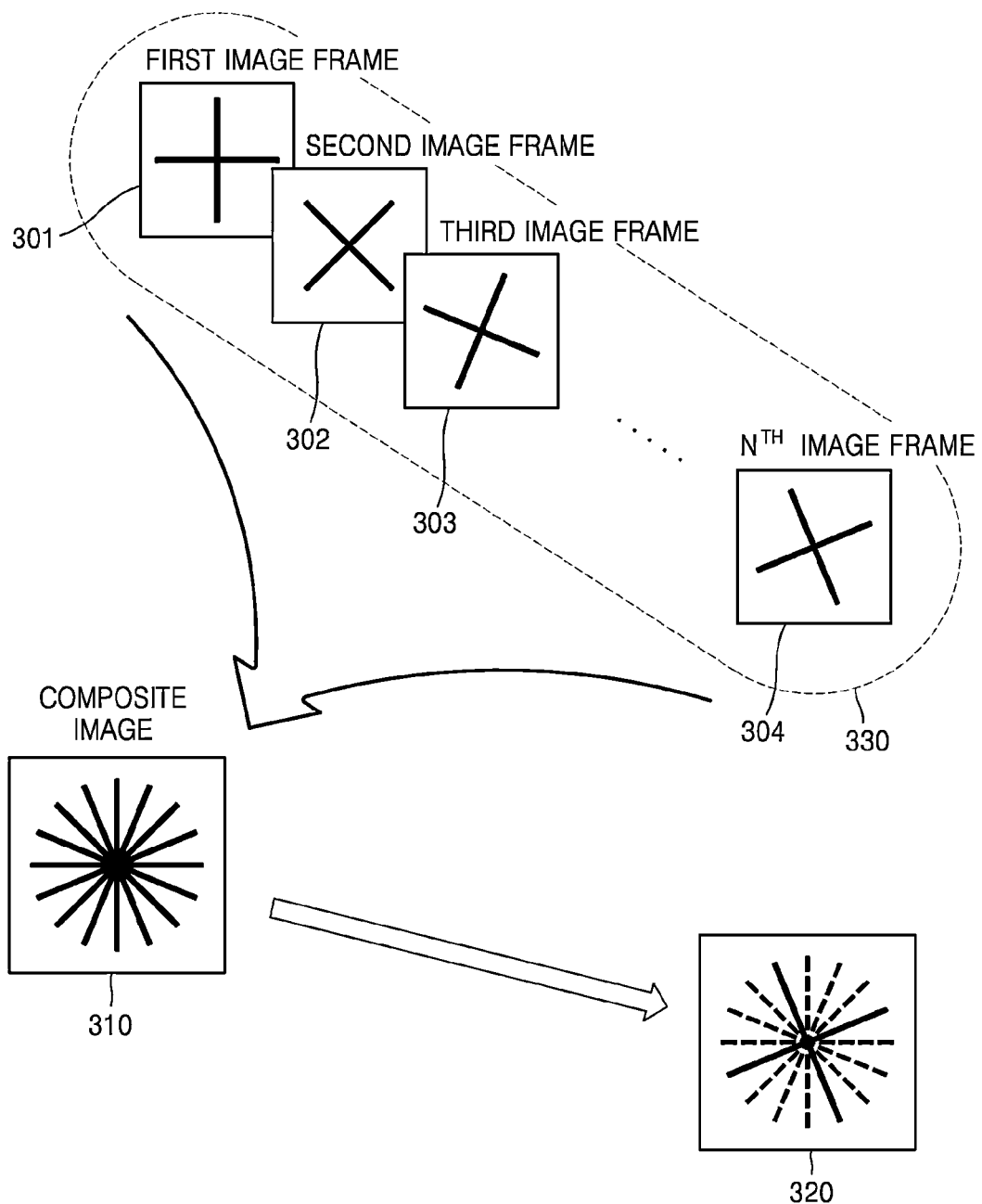
FIG. 3 is a diagram for describing an application of an exemplary embodiment to the medical imaging field.

FIG. 3 is a diagram for describing an application of an exemplary embodiment to the medical imaging field.

In imaging methods, techniques for reducing the amount of time an image is obtained and securing a high resolution of the image have been continuously developed. For example, regarding an MRI imaging method, a radial image obtaining technique for undersampling k-space by using a radial view may be used for successfully reconstructing images even in a sub-sampling environment. As shown in FIG. 3, a radial image obtaining technique for sampling lines extending outward from the center of a k-space instead of sampling the k-space in a lattice pattern could be used for successfully reconstructing images from insufficient data in a dynamic image obtaining method using time-resolved data.

Referring to FIG. 3, image frames 330 obtained by the data obtainer 221 of FIGS. 2A and 2B may have two radial views per frame as illustrated by first, second, and third to nth image frames 301, 302, and 303 to 304. However, the present exemplary embodiment is not limited thereto, and an actual image frame may be a set of undersampled views or image data having low signal-to-noise ratio (SNR).

The composite image generator 230 may generate a composite image 310 by synthesizing obtained image frames, where the composite image 310 has higher resolution than the image frames. However, since the first, second, and third to nth image frames 301, 302, and 303 to 304 are data obtained at different times, the composite image 310 needs to be compensated, to obtain an image corresponding to a particular frame. A medical image 320 shown in FIG. 3 is obtained by compensating the composite image 310 based on the nth image frame 304. By using the imaging method described above, a relatively high-quality image may be obtained in a relatively short period of time.

Figure 4:
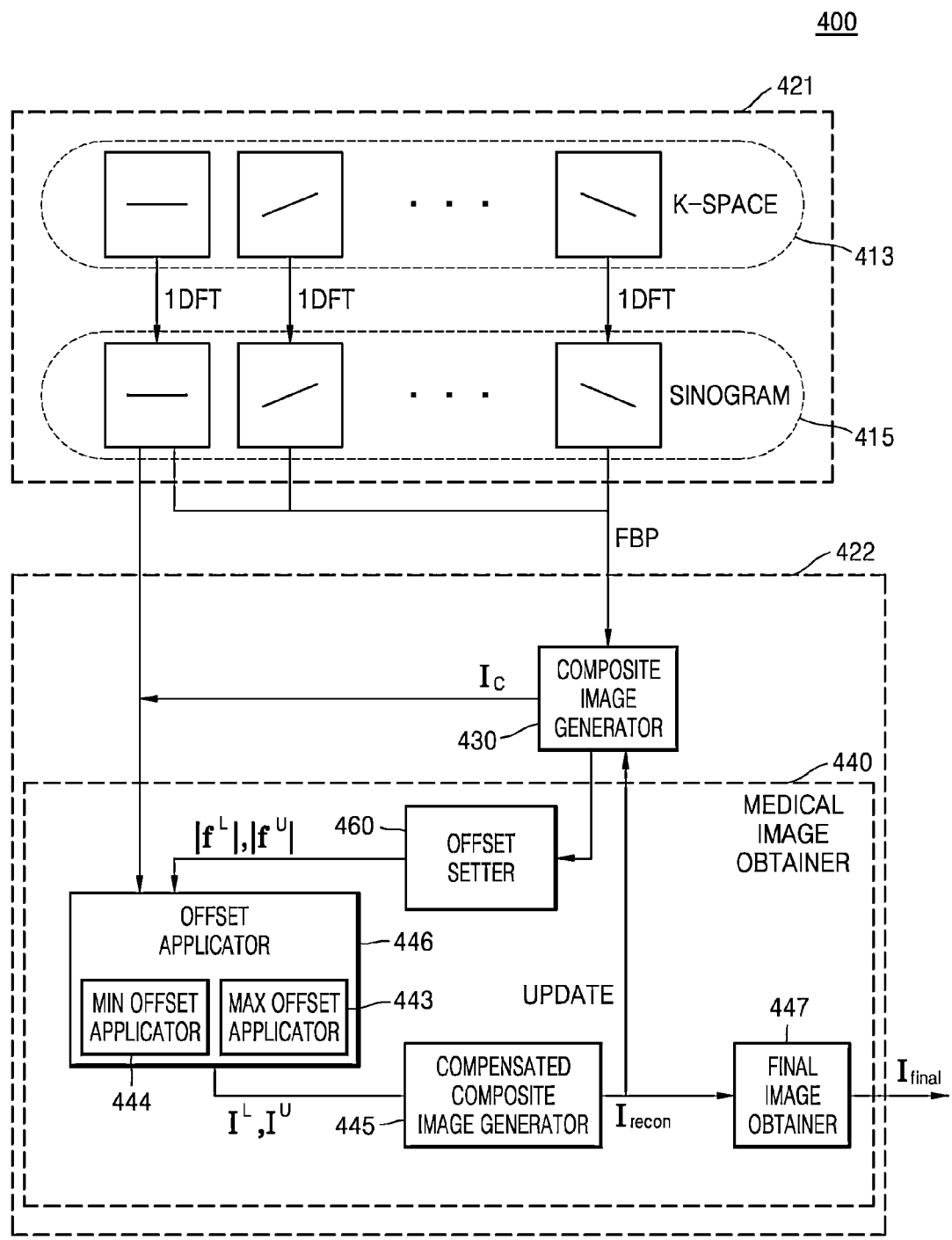
FIG. 4 is a diagram showing operations of a medical diagnostic apparatus according to an exemplary embodiment.

FIG. 4 is a diagram showing operations of a medical diagnostic apparatus 400 according to an exemplary embodiment in detail.

Referring to FIG. 4, the medical diagnostic apparatus 400 includes a data obtainer 421 and a data processor 422 which includes a composite image generator 430 and a medical image obtainer 440. The data obtainer 421, the data processor 422, the composite image generator 430, and the medical image obtainer 440 respectively correspond to the data obtainer 221, the data processor 222, the composite image generator 230, and the medical image obtainer 240 shown in FIGS. 2A and 2B, and thus descriptions thereof are not repeated.

Referring to FIG. 4, a plurality of pieces of k-space data 413, that are raw data generated as the data obtainer 421 captures an image of an object, are transformed via one-dimensional Fourier transform (1DFT), thereby generating image frames 415 including a plurality of sinograms. For example, the k-space data 413 may be generated by the MRI imaging apparatus 110 of FIG. 1 and may be received by the data obtainer 421. The plurality of pieces of k-space data 413 and/or the plurality of image frames 415 may correspond to the plurality of image frames 301 to 304 described above with reference to FIG. 3, and thus descriptions thereof are not repeated.

The composite image generator 430 generates a composite image $I_C$ from the plurality of image frames 415 including the plurality of sinograms, by synthesizing the plurality of image frames 415.

FIG. 4 shows a case in which calculations regarding filtered back projection (FBP) are performed with respect to sinograms to generate the composite image $I_C$.

In detail, FIG. 4 shows operations at a medical image obtainer 440 for obtaining an offset compensated composite image $I_{recon}$ by compensating the composite image $I_C$ by using an arbitrary image frame selected as a reference for reconstructing a medical image and boundary conditions of image signals included in the composite image $I_C$ and obtaining a medical image $I_{final}$ by using the offset compensated composite image $I_{recon}$. The operations at a medical image obtainer 440 shown in FIG. 4 may be performed by the medical image obtainer 240 of FIGS. 2A and 2B.

For example, the medical image obtainer 440 may include an offset setter 460, an offset applicator 446 including a maximum offset applicator 443 and a minimum offset applicator 444, and a compensated composite image generator 445.

The medical image obtainer 440 obtains an offset compensated composite image $I_{recon}$ by compensating a composite image $I_C$ by using a predetermined image frame and boundary conditions of image signals included in the composite image $I_C$ and obtains a medical image $I_{final}$ corresponding to a time point, at which the predetermined image frame is generated, by using the offset compensated composite image $I_{recon}$.

The medical image obtainer 440 may use absolute values of the maximum value $f^U$ and the minimum value $f^L$ of image signals included in the composite image $I_C$ as boundary conditions for compensating the composite image Ic. The offset setter 460 may set a maximum offset $|f^U|$ and a minimum offset $|f^L|$ for setting levels of the image signals included in the composite image $I_C$ to have positive values, based on the maximum value $f^U$ and the minimum value $f^L$ of the image signals included in the composite image $I_C$.

The maximum offset applicator 443 may compensate a composite image, to which the maximum offset $|f^U|$ is applied, by using an image frame, to which the maximum offset $|f^U|$ is applied.

In detail, the maximum offset applicator 443 may apply the maximum offset $|f^U|$ to an image frame corresponding to the composite image $I_C$, such that levels of image signals included in the image frame have positive values, and may apply the maximum offset $|f^U|$ to the composite image $I_C$, such that levels of image signals included in the composite image have positive values.

For example, to reconstruct and generate a medical image captured at a predetermined time point, a composite image $I_C$ corresponding to the predetermined time point may be obtained. In this case, the image frame corresponding to the composite image $I_C$ is a predetermined image frame captured at the predetermined time point. As another example, if a user requests reconstruction of a medical image corresponding to a predetermined time point, a composite image $I_C$ based on an image frame corresponding to the predetermined time point as requested by the user may be generated. Therefore, the medical image obtainer 440 may select an image frame obtained at the predetermined time point as requested by the user from among a plurality of image frames and compensate the composite image $I_C$ based on the selected image frame. In this case, the image frame corresponding to the composite image $I_C$ is an image frame selected based on a request of a user.

The minimum offset applicator 444 may compensate a composite image, to which the minimum offset $|f^L|$ is applied, by using an image frame, to which the minimum offset $|f^L|$ is applied.

In detail, the minimum offset applicator 444 may apply the minimum offset $|f^L|$ to an image frame corresponding to the composite image $I_C$, such that levels of image signals included in the image frame have positive values, and may apply the minimum offset $|f^L|$ to the composite image $I_C$, such that levels of image signals included in the composite image have positive values.

The compensated composite image generator 445 may generate an offset compensated composite image $I_{recon}$ by using a first compensated composite image $I^U$ compensated by the maximum offset applicator 443 and a second compensated composite image $I^L$ compensated by the minimum offset applicator 444.

The medical image obtainer 440 may further include a final image obtainer 447 for obtaining a medical image $I_{final}$ from the offset compensated composite image $I_{recon}$. An HYPR technique that may be applied to the compensated composite image generator 445 of FIG. 4 according to an exemplary embodiment is described below with reference to FIG. 5.

According to an exemplary embodiment, the data processor 422 may repeatedly compensate a composite image by using an image frame and boundary conditions for a number of times, where a compensated composite image compensated in a single compensation may be used as a composite image for a next compensation.

FIG. 4 shows an operation for updating an offset compensated composite image $I_{recon}$ that is generated by using the first compensated composite image $I^U$ compensated by the maximum offset applicator 443 and the second compensated composite image $I^L$ compensated by the minimum offset applicator 444 as a composite image $I_C$ for a next compensation. According to the present exemplary embodiment, by repeatedly compensating and updating a composite image, cross-talk deviation between an actually desired image and the composite image may be eliminated, and thus a misconstruction of a medical image due to a mixture of data of a composite image with an image of a particular frame may be prevented.

According to an exemplary embodiment, the medical image obtainer 440 may apply an HYPR technique to compensate a composite image. The HYPR technique is an imaging technique for reconstructing an image by using a data set including a plurality of image frames and an initial composite image.

Figure 5:
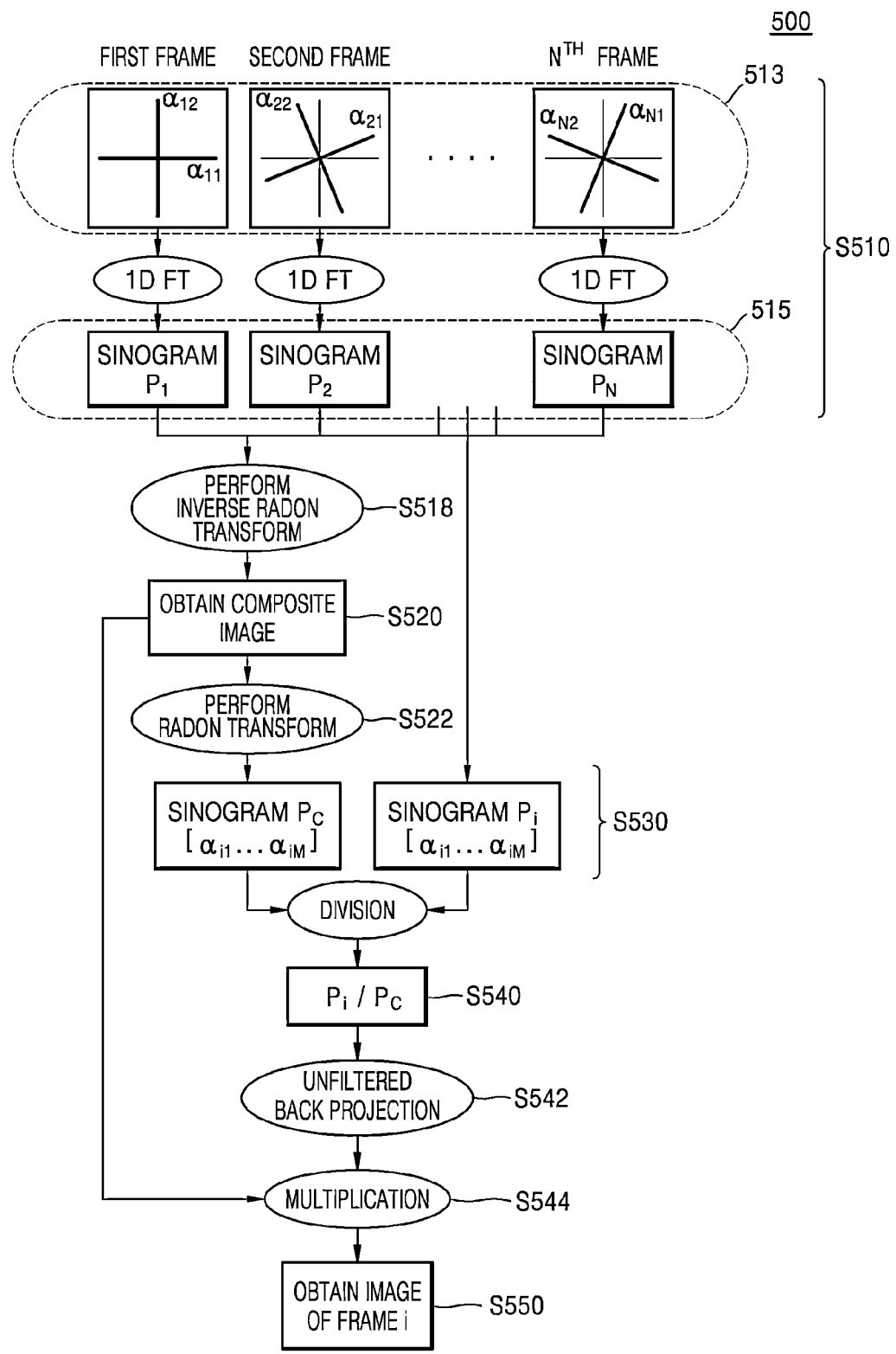
FIG. 5 is a diagram showing operations of a medical diagnostic apparatus to which the HYPR technique is applied for compensating a composite image.

FIG. 5 is a diagram showing operations of a medical diagnostic apparatus 500 to which the HYPR technique is applied. A plurality of pieces of k-space data 513 of FIG. 5 correspond to the plurality of pieces of k-space data 413 of FIG. 4, a plurality of image frames 515 of FIG. 5 correspond to the plurality of image frames 415 of FIG. 4, and an operation S510 for obtaining a plurality of image frames of FIG. 5 may be performed by the data obtainer 421 of FIG. 4. Further, operations S518, S520, and S522 may be performed by the composite image generator 430 of FIG. 4. Operations S530, S540, and S550 of FIG. 5 may be performed by the medical image obtainer 440 of FIG. 4. Therefore, detailed descriptions thereof are not repeated.

As shown in FIG. 5, in the HYPR technique, sinogram data $P_i$ of a particular image frame i to be reconstructed is divided by sinogram data $P_c$ of a composite image (operation S540) and a final image of frame i is obtained (operation S550) by back-projecting (operation S542) a result of the division and multiplying (operation S544) the result of the back-projection by the composite image.

Since the HYPR technique shown in FIG. 5 uses a partially sampled image frame, an image may be obtained in a relatively short period of time. However, the HYPR technique may only be applied to data having positive values. Therefore, to apply the HYPR technique shown in FIG. 5 to a method using complex data, such as the PC method in an MRI system, boundary conditions corresponding to image signals included in a composite image may be used, according to an exemplary embodiment. The present exemplary embodiment provides an improved imaging method for reconstructing an image even when the image has negative values. And more particularly, the present exemplary embodiment provides an improved imaging method for reconstructing an image, even when the image includes complex image data, by separating the complex image data into a real part and an imaginary part.

For example, if it is assumed that a probability distribution of image signals is a normal distribution and the HYPR technique is applied by using boundary conditions of the image signals according to the present exemplary embodiment, the first compensated composite image $I^U$, the second compensated composite image $I^L$, and the offset compensated composite image $I_{recon}$ of FIG. 4 may be expressed as shown in Equations 1 through 3 below, respectively.

$$I^U = \text{real}(f^U - I_C) \times \frac{\text{real}(R^{-1}(Rf^U - S))}{\text{real}(R^{-1}R(f^U - I_C))} + \quad \text{[Equation 1]}$$
$$i \times \text{imag}(f^U - I_C) \times \frac{\text{imag}(R^{-1}(Rf^U - S))}{\text{imag}(R^{-1}R(f^U - I_C))}$$

$$I^L = \text{real}(I_C - f^L) \times \frac{\text{real}(R^{-1}(S - Rf^L))}{\text{real}(R^{-1}R(I_C - f^L))} + \quad \text{[Equation 2]}$$
$$i \times \text{imag}(I_C - f^L) \times \frac{\text{imag}(R^{-1}(S - Rf^L))}{\text{imag}(R^{-1}R(I_C - f^L))}$$

$$I_{recon} = \frac{I^L \times f^U + I^U \times f^L}{I^L + I^U} \quad \text{[Equation 3]}$$

In Equations 1 through 3 above, $f^U$ denotes a maximum offset value for setting levels of image signals included in a composite image to have positive values, $f^L$ denotes a minimum offset value for setting levels of the image signals included in the composite image to have positive values, s denotes a sinogram of a reference image frame for compensation, R denotes a Radon transform, $R^{-1}$ denotes an inverse Radon transform, $I_C$ denotes a composite image, $I^U$ denotes a result of compensating a composite image, to which the maximum offset is applied, by using an image frame, to which the maximum offset is applied, $I^L$ denotes a result of compensating a composite image, to which the minimum offset is applied, by using an image frame, to which the minimum offset is applied.

The offset compensated composite image $I_{recon}$ is compensated by using an image frame and boundary conditions corresponding to image signals included in the composite image. Since the offset compensated composite image $I_{recon}$ is generated by using a first compensated composite image $I^U$ to which the maximum offset is applied and a second compensated composite image $I^L$ to which the minimum offset is applied, the offset compensated composite image $I_{recon}$ may be received by using $I^U$ and $I^L$. However, the equation above is merely an example to help understand the present exemplary embodiment, and the present exemplary embodiment is not limited thereto.

FIGS. 6A, 6B, 6C, and 6D are diagrams for describing a medical image imaging result obtained according to an exemplary embodiment.

Figure 6A:
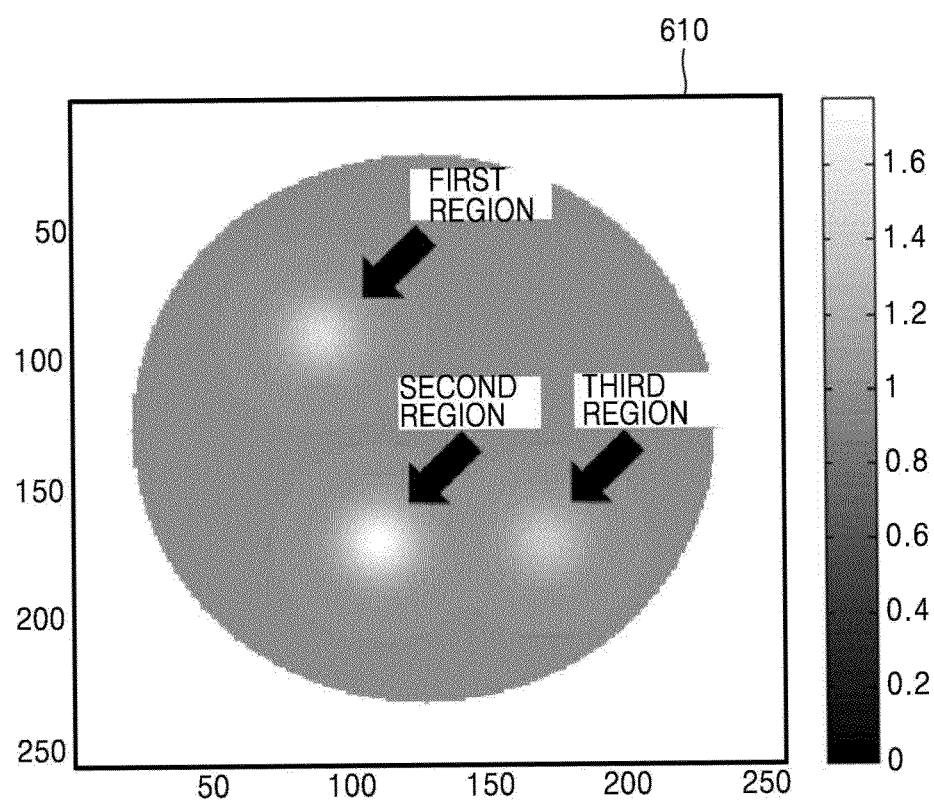
FIGS. 6A, 6B, 6C, and 6D are diagrams for describing a medical image imaging result obtained according to an exemplary embodiment.

Referring to FIG. 6A, a phantom image 610 having sixty four frames and brightness increasing and decreasing according to time frames is shown. The phantom image 610 is an image captured at a resolution of 256*256 pixels.

Figure 6B:
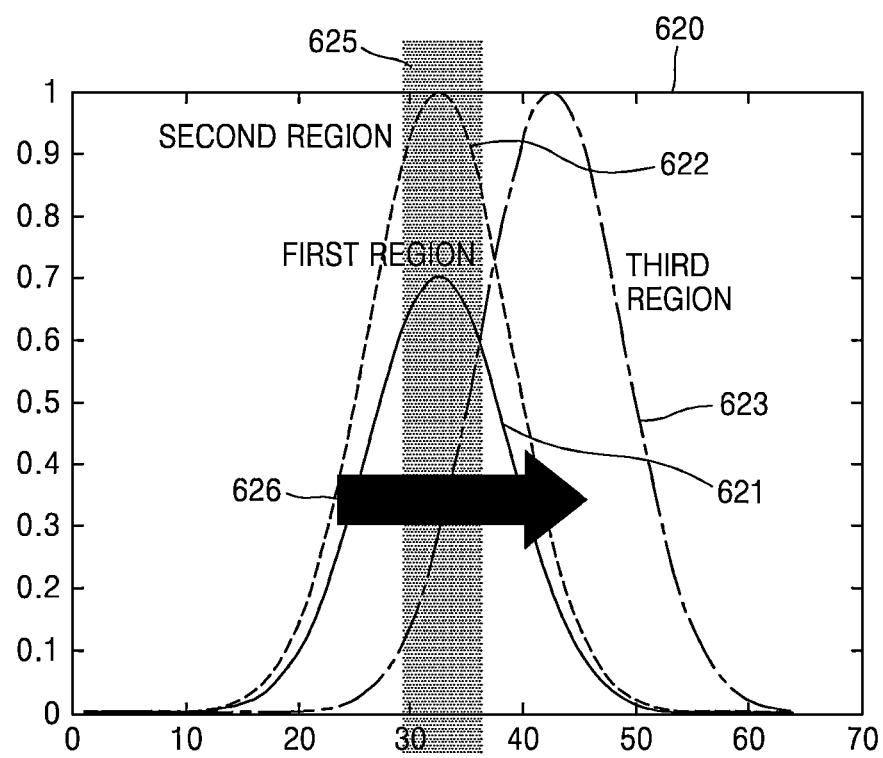

Referring to FIG. 6B, brightness of first, second and third regions of the phantom image 610 in which brightness increases and decreases according to time frames are indicated by curves 621, 622, and 623 of a graph 620, respectively. The x-axis of the graph 620 indicates frames and the y-axis indicates relative brightness. Each frame includes thirty two views. Therefore, a suitable size of a window for obtaining 256 full views in total is eight frames. In other words, a composite image having 256 views in total may be generated by synthesizing eight frames having thirty two views each. A highlighted block in the graph 620 indicates a frame window 625 having eight frames. A composite image is generated by moving the eight frame window 625 from the first through eighth frame section to the fifth-seventh through sixty-fourth frame section, as indicated by an arrow 626.

Figure 6C:
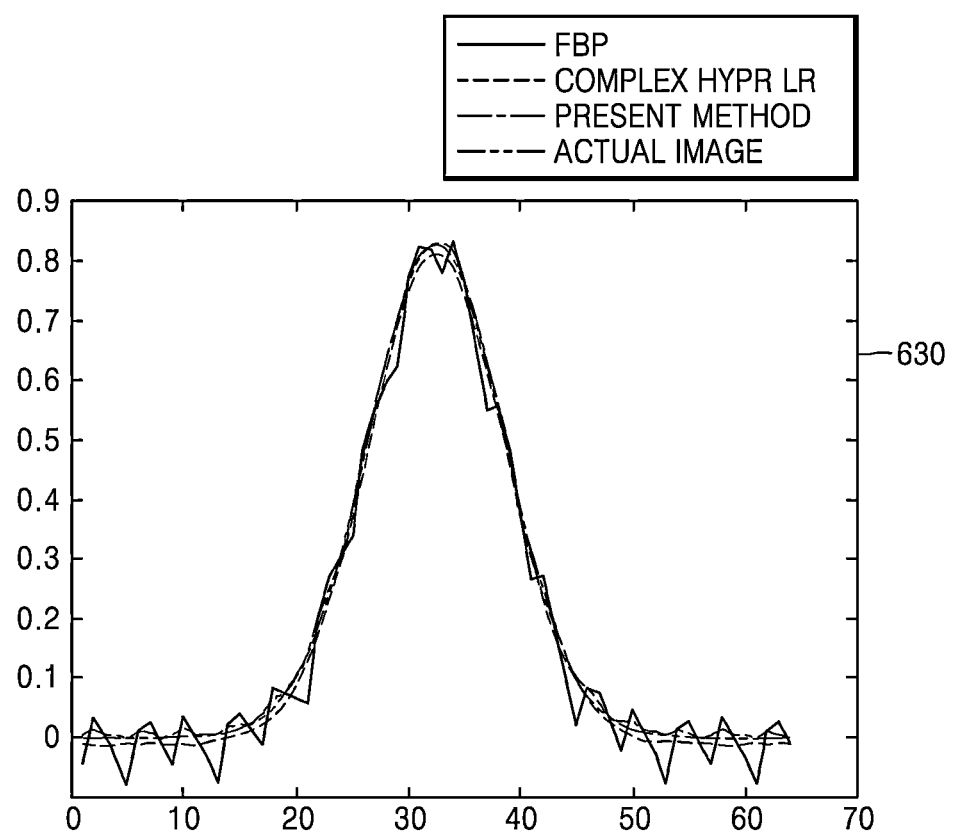
Figure 6D:
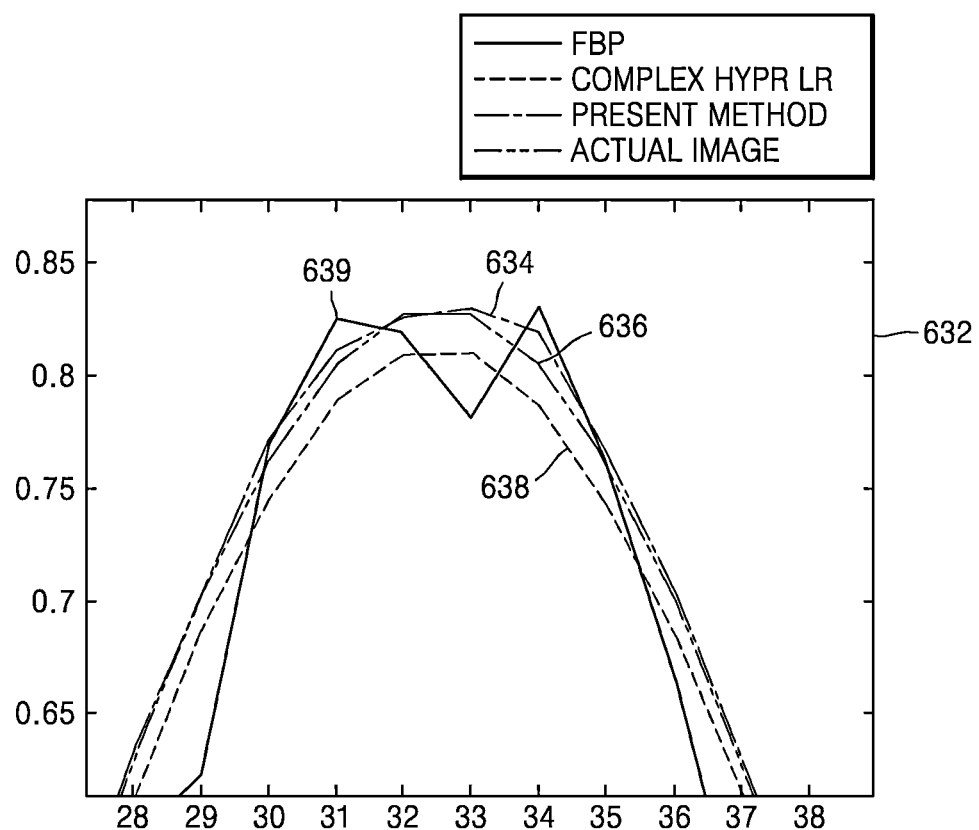

With reference to FIGS. 6C and 6D, the composite image is compensated at the third frame of each window, e.g., the third frame in the first through eight frame section, and a result of repeating composite image compensations for 20 times is indicated by graphs 630 and 632. The graphs 630 and 632 indicate a brightness of a second region in a medical image reconstructed using an imaging method according to the present exemplary embodiment. The x-axis of the graphs 630 and 632 indicates frames and the y-axis indicates relative brightness. The graph 634 shows that the imaging method according to the present exemplary embodiment provides the most similar result to actual data (graph 636), as compared to a complex HYPR local reconstruction (LR) method (graph 638) and FBP method (graph 639).

The complex HYPR LR method is a method for dynamic image reconstruction of radial data by blurring absolute values of an image by using a low pass filter and multiplying the blurred absolute values by original phase values of the image. The complex HYPR LR method enables reconstruction of phase values, but composite image data is mixed into a result of reconstruction. The FBP method is a combination of back projection, which is for adding projection values obtained in a plurality of directions back to a pixel surface, and mathematical filtering processes.

Figure 7:
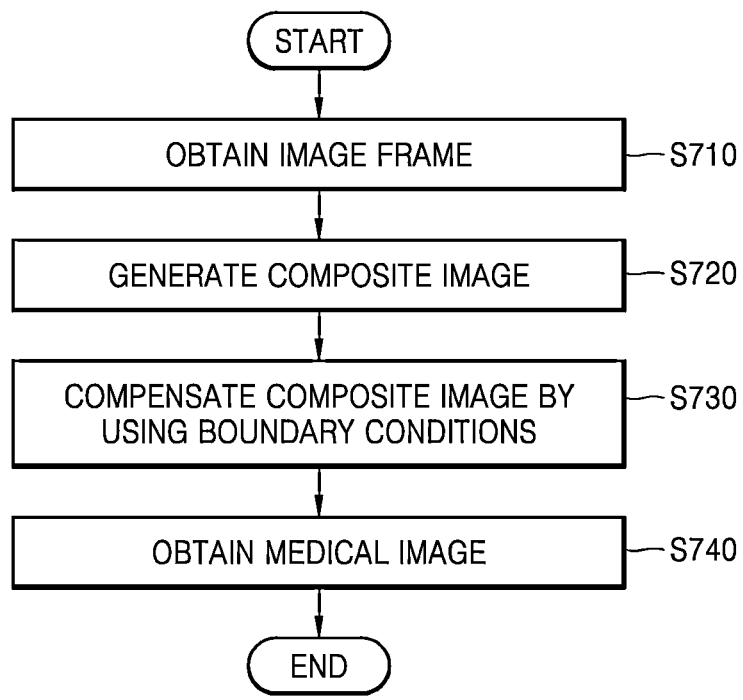
FIG. 7 is a flowchart showing an imaging method according to an exemplary embodiment.

FIG. 7 is a flowchart showing an imaging method 700 according to an exemplary embodiment.

The imaging method 700 shown in FIG. 7 may be performed by the medical diagnostic apparatus 200 described above with reference to FIGS. 2A and 2B operations included in the imaging method 700 may be similar to operations of components of the medical diagnostic apparatus 200. Hereinafter, the imaging method 700 is described in detail with reference to the medical diagnostic apparatus 200 shown in FIGS. 2A and 2B.

Referring to FIG. 7, the medical diagnostic apparatus 200 obtains at least one image frame per at least one view included in a region to be imaged (operation S710). Operation S710 may be performed by the data obtainer 221 of FIGS. 2A and 2B. The medical diagnostic apparatus generates a composite image by using the obtained image frame (operation S720) and compensates the composite image by using the image frame and boundary conditions corresponding to image signals included in the composite image (operation S730). A final medical image is obtained from the compensated composite image (operation S740). Operation S720 may be performed by the composite image generator 230 and operations S730 and S740 may be performed by the medical image obtainer 240 of FIGS. 2A and 2B.

Figure 8:
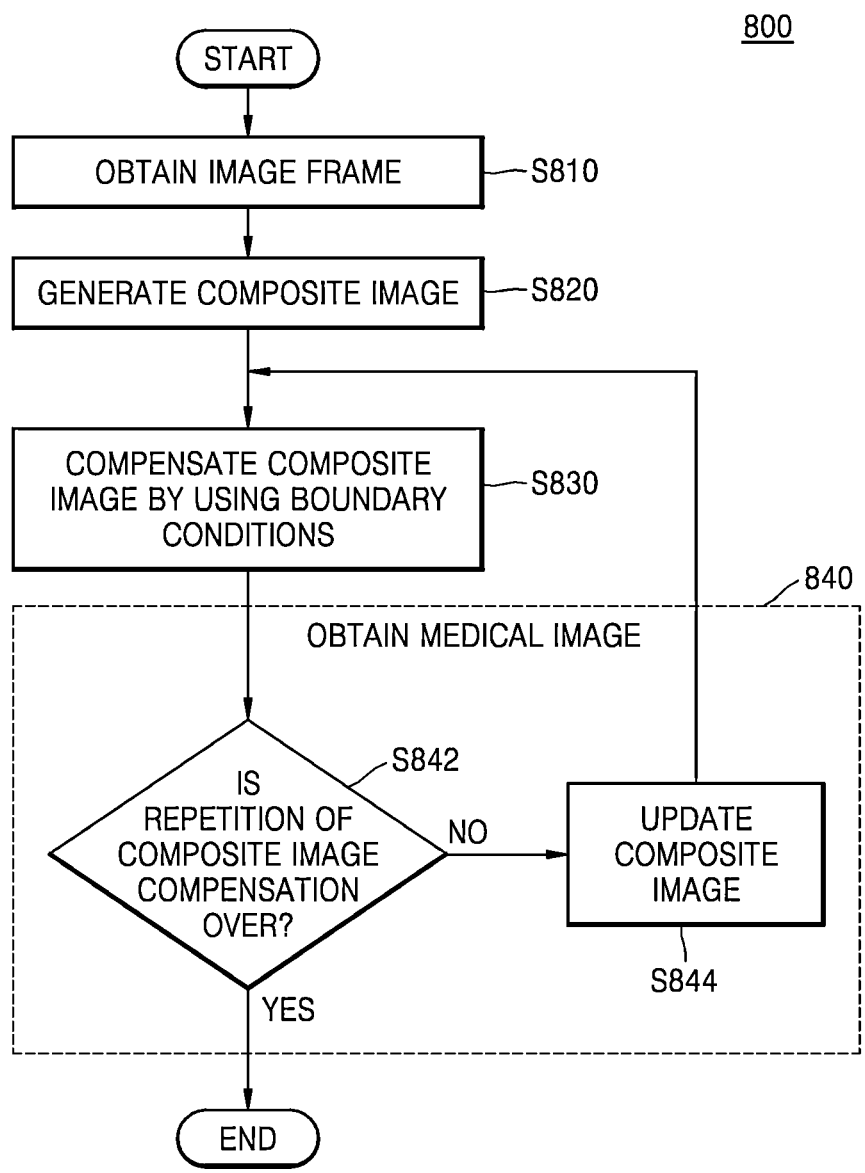
FIG. 8 is a flowchart showing an imaging method according to an exemplary embodiment.

FIG. 8 is a flowchart showing an imaging method 800 according to an exemplary embodiment.

The imaging method 800 shown in FIG. 8 includes operations performed by the data obtainer 221, the composite image generator 230, and the medical image obtainer 240. Operation S810 of FIG. 8 corresponds to operation S710 of FIG. 7, operation S820 of FIG. 8 corresponds to operation S720 of FIG. 7, operation S830 of FIG. 8 corresponds to operation S730 of FIG. 7, and operation S840 of FIG. 8 corresponds to operation S740 of FIG. 7. Therefore, even if omitted below, any of the descriptions of the operations with reference to FIG. 7 above may also apply to the operations shown in FIG. 8.

Referring to FIG. 8, operation S840 for obtaining a medical image performs iterative image compensation by repeating composite image compensations by using image frames and boundary conditions. In operation S842, if it is determined that all of the iterative compensations, for example, 20 cycles, are performed, the method terminates. If it is determined that not all of the iterative compensations are performed, the method proceeds to operation S844 in which a composite image compensated in a single compensation is updated as a composite image for a next compensation. Operation S844 of FIG. 8 corresponds to the operation shown in FIG. 4 in which the offset compensated composite image $I_{recon}$ is updated as a composite image IC. According to the present exemplary embodiment, unnecessary data of a composite image is prevented from being mixed into a reconstructed image by repeatedly performing image compensations as shown in FIG. 8.

Experiment 1

Figure 9A:
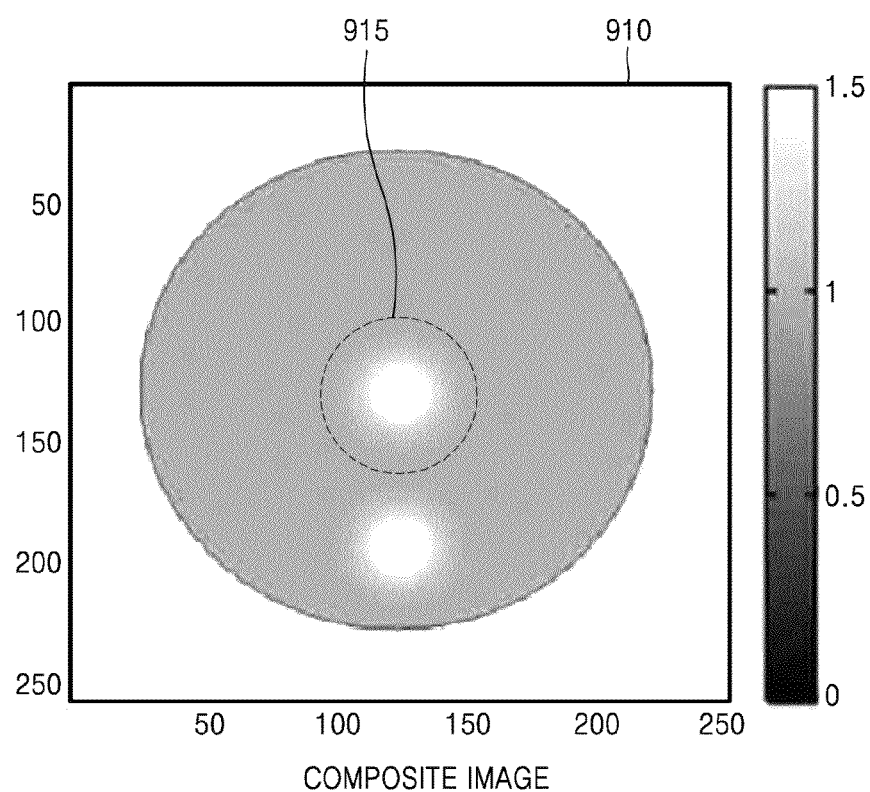
FIGS. 9A, 9B, 9C, and 9D show comparison images obtained as a result of a first simulation.
Figure 9B:
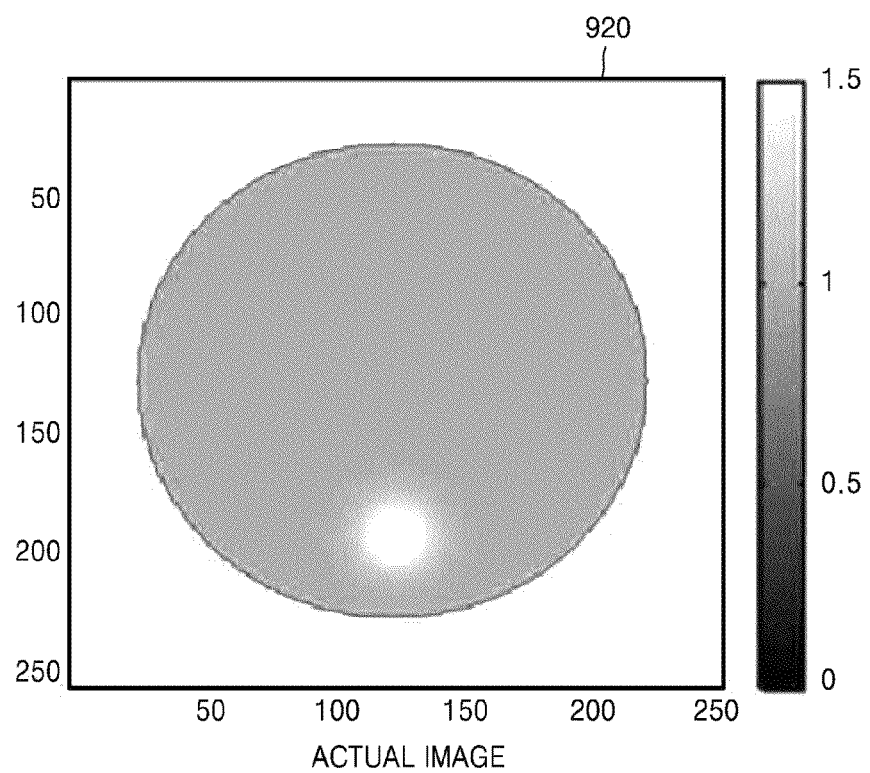
Figure 9C:
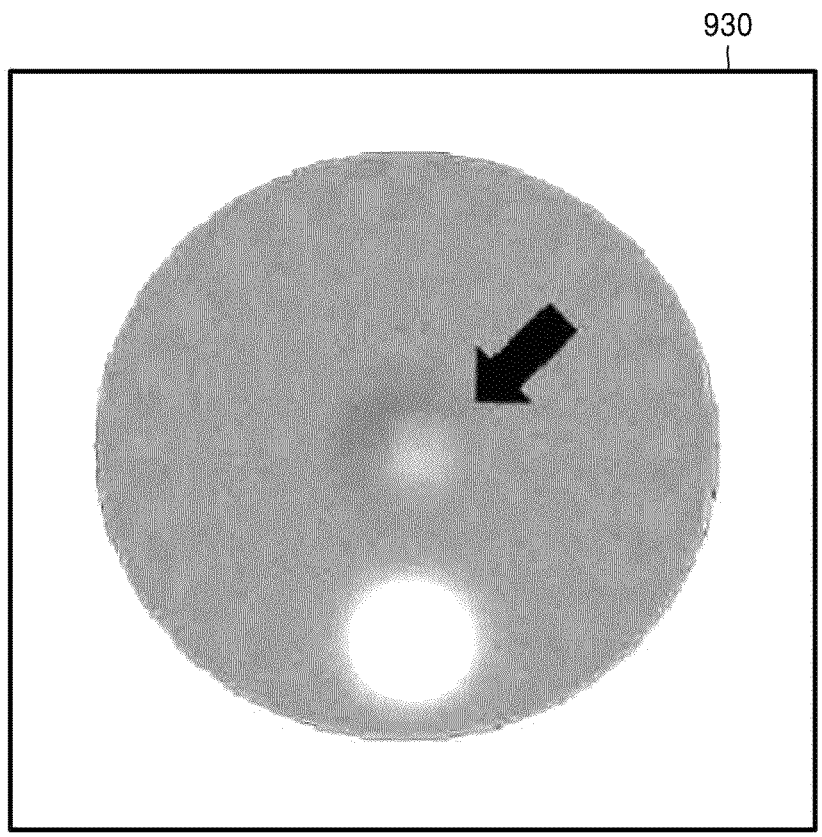
Figure 9D:
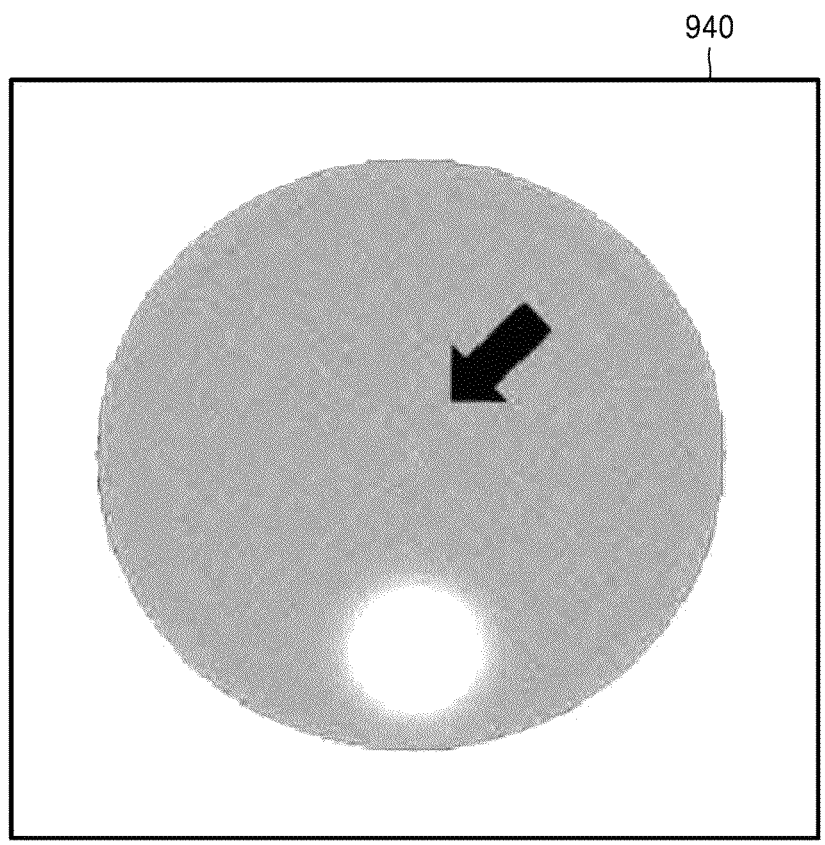

FIG. 9D is a diagram showing an image 940 obtained as a result of a first simulation according to an exemplary embodiment. A composite image 910 and an actual image 920 at a particular frame were set as described below and results of performing an imaging method according to the present exemplary embodiment and the complex HYPR LR method were compared to each other. The number of sampling lines per frame was 50 views.

As shown in FIGS. 9A and 9B, as compared to the actual image 920, the composite image 910 includes extraneous data 915 of other frames.

Therefore, it was necessary to compensate the composite image 910, and an image 930 reconstructed by using the complex HYPR LR method is shown in FIG. 9C. However, although the composite image 910 was compensated to be more like the actual image 920 by using the complex HYPR LR method, there was still a cross-talk error remaining in an area indicated by an arrow, in the image 930.

On the contrary, a cross-talk error was effectively eliminated in the image 940 obtained by performing the imaging method according to the present exemplary embodiment as shown in FIG. 9D. The image 940 was obtained by repeating composite image compensations for 20 times.

Experiment 2

Figure 10A:
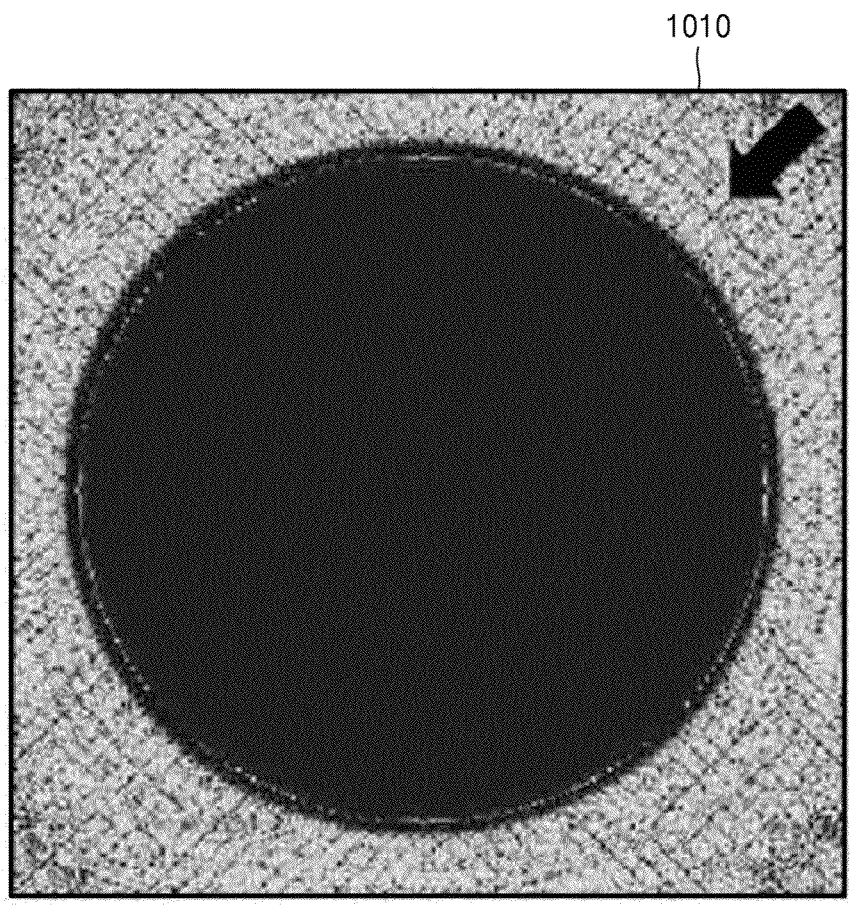
FIGS. 10A and 10B show comparison images obtained as a result of a second simulation.
Figure 10B:
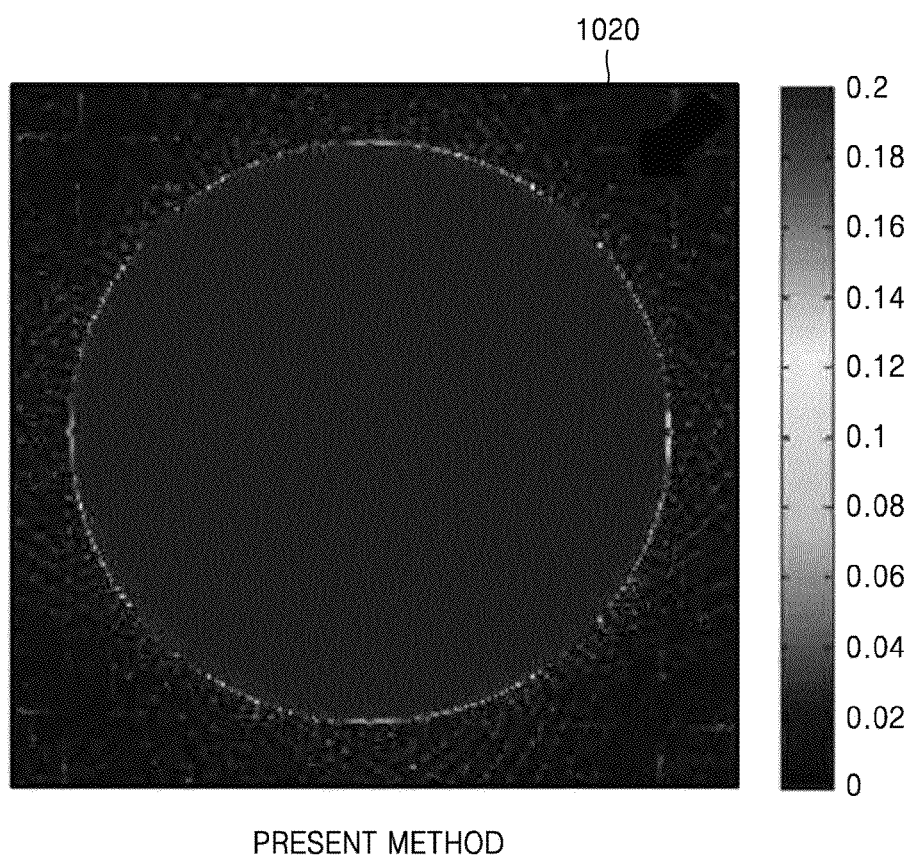

FIGS. 10A and 10B show images obtained as a result of a second simulation according to an exemplary embodiment.

As shown in FIGS. 10A and 10B, an image 1020 obtained as a result of performing the imaging method according to an exemplary embodiment included substantially fewer streaking artifacts in an area indicated by an arrow than an image 1010 obtained as a result of performing the complex HYPR LR method.

Experiment 3

FIGS. 11A, 11B, 11C, and 11D show images 1110, 1120, 1130, and 1140 obtained as a result of a third simulation according to an exemplary embodiment, and images 1115, 1125, 1135, and 1145 which are generated to highlight flows by multiplying the image corresponding to the absolute values of the obtained images and phase differences, in correspondence to the images 1110, 1120, 1130, and 1140, respectively.

To confirm an efficiency of the imaging method according to the present exemplary embodiment regarding an actual image, the carotid artery and the jugular vein in the neck of a human were imaged. The reference numeral 1110 denotes an actual image thereof. Parameters used in the third simulation are as follows:

TE (echo time)=5 ms
VENC (Velocity ENCoding)=115 cm/s regarding an entire image
Thickness=6 mm
FOV (Field of View)=220 mm$^2$
Lattice Size=256×256
32 views sampled per cycle
Windows=4
One reading per heartbeat cycle
Gating with ECG triggering For easy recognition of parts of the human body corresponding to tissue of the actual image 1110, an image 1115, which emphasizes blood flow by combining a sectional image of a human neck with the actual image 1110, is shown. Further, images 1125, 1135, and 1145, which are images emphasizing blood flow by combining sectional image of a human neck with images 1120, 1130, and 1140 that are obtained as results of performing the FBP method, the complex HYPR LR method, and the imaging method according to an exemplary embodiment, respectively, are shown.

Comparing portions of images indicated by arrows in FIGS. 11B, 11C, and 11D, the image 1140 that was obtained as a result of performing the imaging method according to an exemplary embodiment includes substantially fewer streaking artifacts than the images 1120 and 1130 that were obtained as results of performing the FBP method and the complex HYPR LR method.

Although a few exemplary embodiments have been shown and described, it would be appreciated by those skilled in the art that various changes in form and detail may be made in these exemplary embodiments without departing from the spirit and scope of the disclosure, the scope of which is defined by the claims and their equivalents.

What is claimed is:

1. An imaging method for obtaining a medical image by a medical imaging apparatus, the imaging method comprising:
    obtaining image frames based on k-space data which is acquired from an imaging region of an object and includes complex data values;
    generating a composite image by using the image frames;
    compensating the composite image by using one image frame, of the image frames, and boundary values corresponding to image signals included in the composite image; and
    obtaining the medical image by using the compensated composite image,
    wherein the boundary values include a maximum value and a minimum value of the image signals included in the composite image, and
    the compensating the composite image includes adjusting values of the image signals of the composite image based on the maximum value and the minimum value of the image signals such that the values of the image signals of the composite image contain only positive values.

2. The imaging method of claim 1, wherein
    the compensating the composite image comprises setting a maximum offset value and a minimum offset value, based on the maximum value and the minimum value of the image signals included in the composite image; and
    applying the maximum offset value and the minimum offset value to the image signals included in the composite image, so that the values of the image signals included in the composite image are adjusted to have the positive values.

3. The imaging method of claim 2, wherein the compensating the composite image comprises:
    applying the maximum offset value to the one image frame, so that levels of image signals included in the one image frame have positive values;
    compensating the composite image, to which the maximum offset value is applied, by using the one image frame, to which the maximum offset value is applied;
    applying the minimum offset value to the one image frame, so that the levels of image signals included in the image frame have positive values;
    compensating the composite image, to which the minimum offset value is applied, by using the one image frame, to which the minimum offset value is applied; and
    generating the compensated composite image by using the compensated composite image to which the maximum offset value is applied and the compensated composite image to which the minimum offset value is applied.

4. The imaging method of claim 1, wherein the obtaining the medical image comprises repeatedly compensating the composite image by using the one image frame and the boundary values for a number of times, and
    the composite image compensated in a single compensation is updated as a composite image for a next compensation.

5. The imaging method of claim 1, wherein the composite image is compensated by using a highly-constrained projection reconstruction (HYPR) method.

6. The imaging method of claim 1, wherein the obtaining the image frames comprises obtaining the image frames of radial views included in the imaging region.

7. The imaging method of claim 1, wherein the medical imaging apparatus comprises a magnetic resonance imaging (MRI) apparatus, and
    the image frames comprise complex image data.

8. The imaging method of claim 1, wherein, when $$I^U = \text{real}(f^U - I_C) \times \frac{\text{real}(R^{-1}(Rf^U - S))}{\text{real}(R^{-1}R(f^U - I_C))} +$$
$$i \times \text{imag}(f^U - I_C) \times \frac{\text{imag}(R^{-1}(Rf^U - S))}{\text{imag}(R^{-1}R(f^U - I_C))}$$

and $$I^L = \text{real}(I_C - f^L) \times \frac{\text{real}(R^{-1}(S - Rf^L))}{\text{real}(R^{-1}R(I_C - f^L))} +$$
$$i \times \text{imag}(I_C - f^L) \times \frac{\text{imag}(R^{-1}(S - Rf^L))}{\text{imag}(R^{-1}R(I_C - f^L))}$$

a compensated image $I_{recon}$ satisfies $$I_{recon} = \frac{I^L \times f^U + I^U \times f^L}{I^L + I^U},$$

where $f^U$ is a maximum offset value for setting the values of the image signals included in the composite image to have positive values,
$f^L$ is a minimum offset value for setting the values of the image signals included in the composite image to have positive values,
s is a sinogram of a reference image frame for compensation,
R is a Radon transform,
R−1 is an inverse Radon transform,
$I_C$ is the composite image,
$I^U$ is a result of compensating the composite image, to which the maximum offset is applied, by using the one image frame, to which the maximum offset is applied, and
$I^L$ is a result of compensating the composite image, to which the minimum offset is applied, by using the one image frame, to which the minimum offset is applied.

9. A medical diagnostic apparatus comprising:
    a data obtainer, which obtains image frames based on k-space data which is acquired from an imaging region of an object and includes complex data values; and
    a data processor, which processes the obtained image frames and obtains a medical image,
    wherein the data processor comprises:
    a composite image generator, which generates a composite image by using the image frames; and
    a medical image obtainer, which compensates the composite image by using one image frame, of the image frames, and boundary values corresponding to image signals included in the composite image, and obtains the medical image by using the compensated composite image,
    wherein the boundary values include a maximum value and a minimum value of the image signals included in the composite image, and
    the compensating the composite image includes adjusting values of the image signals of the composite image based on the maximum value and the minimum value of the image signals such that the values of the image signals of the composite image contain only positive values.

10. The medical diagnostic apparatus of claim 9, wherein the medical image obtainer comprises:
an offset setter which sets a maximum offset value and a minimum offset value, based on the maximum value and the minimum value of the image signals included in the composite image; and
an offset applicator Which applies the maximum offset value and the minimum offset value to the image signals included in the composite image, so that the values of the image signals included in the composite image are adjusted to have the positive values.

11. The medical diagnostic apparatus of claim 10, wherein the offset applicator comprises:
a maximum offset applicator, which applies the maximum offset value to the one image frame and to the composite image, so that the levels of image signals included in the one image frame and in the composite image have positive values, and compensates the composite image, to which the maximum offset value is applied, by using the one image frame, to which the maximum offset value is applied;
a minimum offset applicator, which applies the minimum offset value to the one image frame and to the composite image, so that the levels of image signals included in the one image frame and in the composite image have positive values, and compensates the composite image, to which the minimum offset value is applied, by using the one image frame, to which the minimum offset value is applied; and
a compensated composite image generator, which generates the compensated composite image by using the compensated composite image to which the maximum offset value is applied and the compensated composite image to which the minimum offset value is applied.

12. The medical diagnostic apparatus of claim 9, wherein the medical image obtainer repeatedly compensates the composite image by using the one image frame and the boundary values for a number of times, and
the composite image compensated in a single compensation is updated as a composite image for a next compensation.

13. The medical diagnostic apparatus of claim 9, wherein the medical image obtainer applies a highly-constrained projection reconstruction (HYPR) method for compensating the composite image.

14. The medical diagnostic apparatus of claim 9, wherein the data obtainer obtains the image frames of radial views included in the imaging region.

15. The medical diagnostic apparatus of claim 9, wherein the medical diagnosis apparatus comprises a magnetic resonance imaging (MRI) apparatus, and
the image frames comprise complex image data.

16. The medical diagnostic apparatus of claim 9, wherein, when $$I^U = \text{real}(f^U - I_C) \times \frac{\text{real}(R^{-1}(Rf^U - S))}{\text{real}(R^{-1}R(f^U - I_C))} +$$

$$i \times \text{imag}(f^U - I_C) \times \frac{\text{imag}(R^{-1}(Rf^U - S))}{\text{imag}(R^{-1}R(f^U - I_C))}$$

and $$I^L = \text{real}(I_C - f^L) \times \frac{\text{real}(R^{-1}(S - Rf^L))}{\text{real}(R^{-1}R(I_C - f^L))} +$$

$$i \times \text{imag}(I_C - f^L) \times \frac{\text{imag}(R^{-1}(S - Rf^L))}{\text{imag}(R^{-1}R(I_C - f^L))}$$

a compensated image $I_{recon}$ satisfies $$I_{recon} = \frac{I^L \times f^U + I^U \times f^L}{I^L + I^U},$$

where $f^U$ is the maximum offset value for setting the levels of the image signals included in the composite image to have positive values,
$f^L$ is the minimum offset value for setting the levels of the image signals included in the composite image to have positive values,
s is a sinogram of a reference image frame for compensation,
R is a Radon transform,
R−1 is an inverse Radon transform,
$I_C$ is the composite image,
$I^U$ is a result of compensating the composite image, to which the maximum offset is applied, by using the one image frame, to which the maximum offset is applied, and
$I^L$ is a result of compensating the composite image, to which the minimum offset is applied, by using the one image frame, to which the minimum offset is applied.

17. A non-transitory computer-readable recording medium having recorded thereon a computer program which, when executed by a computer, causes the computer to execute the method of claim 1.

18. An apparatus comprising:
a scanner which obtains image signals of image frames based on k-space data which is acquired from an imaging region and includes complex data values;
a processor which is programmed to perform operations of:
generating a composite image from the image frames,
determining a maximum signal value and a minimum signal value of the image signals of the composite image,
compensating the composite image based on a selected image frame and the determined maximum and minimum signal values by adjusting signal values of the image signals of the composite image such that the values of the image signals of the composite image contain only positive values, and
obtaining a final image from the compensated composite image; and
an output device which outputs the final image,
wherein the selected image frame is one of the images frames which is selected to be used in the compensating.

19. The apparatus of claim 18, wherein the compensating comprises:
determining a first offset value based on the maximum signal value; and
determining a second offset value based on the minimum signal value;
offsetting the signal values of the composite image and of the selected image frame to contain only positive values by:
subtracting the signal values of the composite image and of the selected image frame from the first offset value, respectively, and adding the signal values of the composite image and of the selected image frame to the second offset value, respectively.

20. The apparatus of claim 19, wherein the compensating further comprises:
  compensating the composite image, which is offset by the first offset value, based on the selected image frame, which is offset by the first offset value, to obtain a first compensated composite image; and
  compensating the composite image, which is offset by the second offset value, based on the selected image frame, which is offset by the second offset value, to obtain a second compensated composite image, and
  wherein the obtaining comprises reconstructing the final image from the first and second compensated composite images.

* * * * *